United States Patent [19]

Feaster

[11] 4,418,431

[45] Dec. 6, 1983

[54] INTRAOCULAR LENS

[76] Inventor: Fred T. Feaster, 800 8th Ave., Suite 234, Ft. Worth, Tex. 76104

[21] Appl. No.: 331,645

[22] Filed: Dec. 17, 1981

[51] Int. Cl.$^3$ ............................ A61F 1/16; A61F 1/24
[52] U.S. Cl. .......................................................... 3/13
[58] Field of Search .......................................... 3/13, 1

[56] References Cited

U.S. PATENT DOCUMENTS

| | | | |
|---|---|---|---|
| 4,159,546 | 7/1979 | Shearing | 3/13 |
| 4,174,543 | 11/1979 | Kelman | 3/13 |
| 4,242,760 | 1/1981 | Rainin | 3/13 |
| 4,254,510 | 3/1981 | Tennant | 3/13 |
| 4,338,687 | 7/1982 | Rainin | 3/13 |
| 4,377,873 | 3/1983 | Reichert | 3/13 |

Primary Examiner—Ronald L. Frinks
Attorney, Agent, or Firm—Wofford, Fails & Zobal

[57] ABSTRACT

An intraocular insert suitable for use as an artificial lens implant in the anterior or posterior chamber of a human eye comprising a circular lens body having two position fixation members extending from opposite sides of the periphery of the lens body. The two fixation members are of similar shape but are asymmetrically arranged relative to the circular lens body. Each of the fixation members comprises an arm portion having a base joined to the periphery of the lens body with said arm portion extending from said lens body, an elbow, and an elongated outward-convex seating portion having a first end joined to said arm portion by said elbow and an opposite free end extending in a direction such that said elongated outward-convex seating portion is outward of said arm portion relative to said lens body. Each arm portion is generally parallel to a line tangent to said lens body. Said arm portions of said two fixation members extend from said lens body in opposite directions relative to each other. Said free ends of said elongated outward-convex seating portions extend in opposite directions relative to each other. Each elongated outward-convex seating portion defines an acute angle relative to its arm portion.

46 Claims, 11 Drawing Figures

INTRAOCULAR LENS

BACKGROUND OF THE INVENTION

1. Field of the Invention

The present invention relates to an intraocular lens which is an artificial optical implant device, used as a replacement for the naturally occurring human lens, when the naturally occurring human lens has been removed. The intraocular lens device after implantation, then serves as a means for optical correction of the eye in replacement of the naturally occurring lens.

2. Description of the Prior Art

Surgical implantation of an intraocular lens after the removal of the natural human lens is a method of visual correction now well established as successful in the field of Ophthalmology. The prior art of intraocular lenses involves many different lens designs which rely on various methods of fixation and stabilization of the implant within the eye such that the central or medial lens body is held in a stable position in relation to the pupil and visual axis of the eye. The type of intraocular lens is classified by location of its implantation within the eye, basically: anterior chamber, iris plane and posterior chamber.

The types of intraocular lens designs, classified according to method of fixation within the eye are:
1. Anterior chamber—Scleral spur fixation
2. Iris plane—Iris fixation
3. Iris plane—Iridocapsular fixation
4. Posterior chamber—Iris fixation
5. Posterior chamber—Capsular fixation
6. Posterior chamber—Cilliary sulcus fixation.

Fixation of the intraocular lens may be accomplished by:
1. Three points of touch of the lens device with the tissue providing three point fixation.
2. Four points of tissue touch with the lens device giving four points fixation.
3. Tissue touch in broad arcs with generally curving loops.
4. "Clipping" of the lens to the iris.
5. Suturing of the lens to the iris.
6. Placement of the fixation portions of the lens device within the posterior capsular envelope or bag which then develops adhesions around the portions of the lens device.

The first three methods of fixation, that is, three point, four point or broad arcs of fixation rely upon pressure against the tissue at those points for immobilization of the lens device. This point contact-pressure method of fixation can be used in the anterior chamber in the scleral spur region and the posterior chamber in the cilliary sulcus region.

Intraocular lenses may be used for both primary implantation, that is implantation at the time of initial removal of the natural human lens, or in secondary implantation, that is as a second, separate surgical procedure after the natural human lens has been previously removed in an earler different surgical procedure. Some of the currently available intraocular lenses may be used in either primary implantation or secondary implantation.

Currently available intraocular lens designs provide a variable degree of symmetry and flexibility in the overall design and in the fixation parts which serve to hold the central optical body in position with respect to the pupil and visual axis. As is known to those practiced in the art, a certain degree of flexibility is desirable since it reduces many problems, such as postoperative tenderness, allows for decreased tissue irritation within the eye when the eye undergoes various flexions during natural movement and reduces possibly injury. It is also well known, however, that excessive flexibility in the lens fixation can be a detriment, causing in its excessive flexibility, movement of the lens with resultant tissue irritation, chronic inflamation and damage to the eye with resultant eventual failure of the implant to be tolerated by the eye, causing possible visual loss and possibly requiring removal of the implant.

Currently available models and styles of intraocular lenses are such that they may be generally of solid one piece construction of one material or generally two or three types of material, the central optical body being of one material, such as polymethylmethacrylate, the peripheral fixation parts being of a different material, such as prolene, with the materials being joined to the central optical body mechanically.

There are various surgical techniques to those practiced in the art which can be used to safely remove the naturally occurring human lens. These surgical techniques are one of two general types:
1. Intracapsular lens removal, that is, removal of the human lens in its entirety in one piece with the lens capsule remaining whole and intact and removed completely from the eye.
2. Extracapsular lens removal, that is, removal of the lens in which the integrity of the capsule is intentionally and deliberately broken with the lens being removed in piecemeal fashion by one of several techniques using to a variable degree expression and/or fragmentation of the lens material and aspiration of the lens material with the intention of leaving the capsular "bag" or more particularly, the posterior capsule, intact and in the eye.

SUMMARY OF THE INVENTION

It is an object of the present invention to provide an intraocular lens suitable for use both in the anterior and posterior chamber of the eye.

It is a further object of the present invention to provide an intraocular lens with peripheral fixation members which provide sufficient flexibility to avoid the problem of tenderness and to allow safe implantation into the posterior chamber of the eye and also to have sufficient rigidity to allow adequate fixation of the intraocular lens within the anterior chamber of the eye.

The intraocular lens comprises a circular lens body having first and second position fixation members extending form opposite sides of the periphery of said lens body. Each of said first and second position fixation members comprises an arm portion having a base joined to the periphery of said circular lens body with said arm portion extending from said lens body, an elbow, and an elongated outward-convex seating portion having a first end joined to said arm portion by said elbow and an opposite free end extending in a direction such that said elongated outward-convex seating portion is outward of said arm portion relative to said lens body. The two bases of said arm portions of said first and second position fixation members are located to allow a straight line passing through the center of said circular lens body to pass through said two bases.

The arm portions of said first and second position fixation members extend from said lens body in opposite directions relative to each other. The free ends of said elongated outward-convex seating portions extend in opposite directions relative to each other. Each elongated outward-convex seating portion defines an acute angle relative to its arm portion. Each position fixation member is relatively small in cross-section and resilient such that its arm portion may be moved toward said circular lens body and its elongated outward-convex seating portion may be moved toward its arm portion and hence toward said lens body.

In another aspect each arm portion comprises a straight portion generally parallel to a line tangent to said lens body.

BRIEF DESCRIPTION OF THE DRAWINGS

In all Figs. showing the lens implanted in the eye, it is to be understood that the natural human lens has been removed.

DESCRIPTION OF THE PREFERRED EMBODIMENTS

Figure 1:
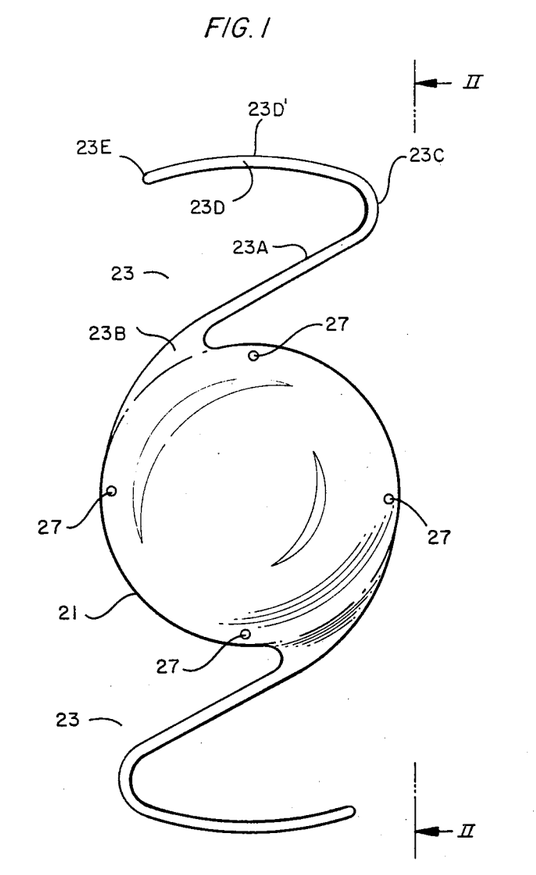
FIG. 1 is a top plan view of the intraocular lens of the present invention.
Figure 2:
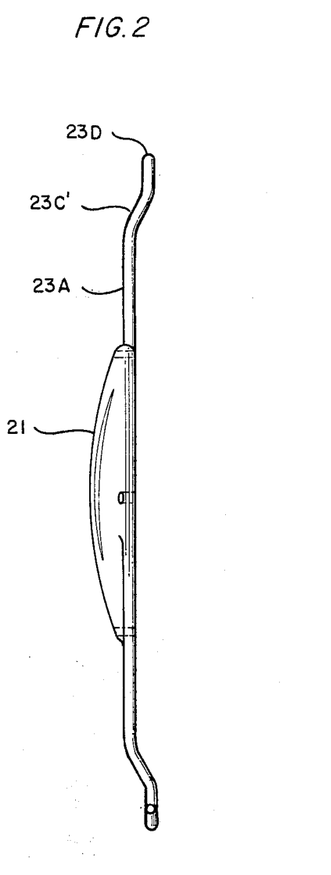
FIG. 2 is a side view of the lens of FIG. 1 as seen from lines 2—2 thereof.
Figure 3:
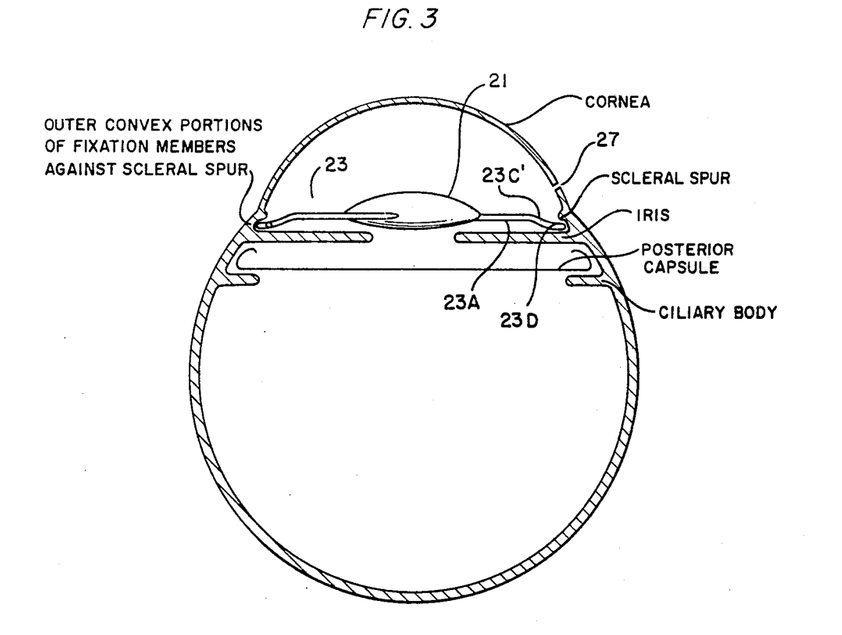
FIG. 3 is a simplified schematic sectional view of an eye with the lens of the present invention implanted in the anterior chamber.
Figure 4:
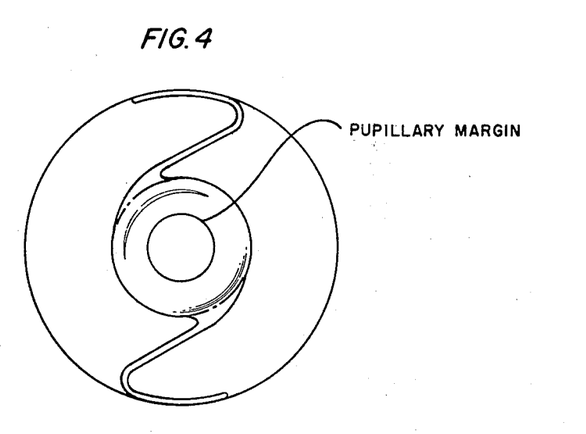
FIG. 4 is a front view of the lens as seen in position in the anterior chamber.
Figure 5:
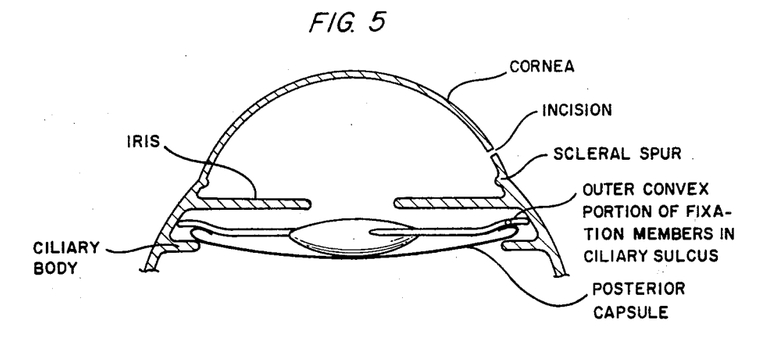
FIG. 5 is a partial simplified schematic sectional view of an eye with the lens of the present invention implanted in the posterior chamber with its fixation members in the ciliary sulcus.

Referring now to FIGS. 1 and 2, the intraocular lens comprises a circular, transparent central or medial lens body 21 of a biconvex or convex planar shape. Extending outwardly from opposite sides of the periphery of the lens body 21 are two position fixation loops or members 23. The fixation members 23 are identical in shape but are asymmetrically arranged relative to the lens body 21. Each fixation member 23 comprises three structural components. Referring to the upper fixation member 23 shown in FIG. 1, it comprises a proximal arm 23A which extends generally diagonally to the lens body 21 and is joined proximally to the lens body at a broader base 23B which tapers to a generally thin arm. As shown, the thin arm 23A is generally parallel to a straight line tangent to the lens body 21. The thin arm 23A continues curving rather sharply back on itself in a "hairpin" figuration at the area of an elbow 23C. The elbow 23C then continues in a general broad outward-convex curve portion 23D which comprises the fixation curve or seating curve of the member 23. As the proximal arm 23A approaches the elbow 23B of the member 23, a stepping off or "vaulting" occurs as shown at 23C' in FIG. 2 such that the outward-convex portion 23D of member 23 is non-coplanar with the arm portion 23A and the lens body 21. The outer portion 23D of member 23 is convex outward providing a broad base fixation area along its outer-convex curvature edge 23D' for seating against or engaging the tissue of the eye. Thus overall fixation of the lens is provided by broad contact of the outward-convex portions 23D of the two fixation members 23 giving two broad bases of tissue contact and fixation. The lens may be inserted within the eye through an incision 27 (see FIG. 3) formed through the cornea in the usual fashion for cataract surgery. The lens body 21 is provided with four peripheral holes 27 for use for manipulation of the lens within the eye.

The specific dimensions of the intraocular lens may vary, however, in one embodiment it may have the following dimensions. The diameter of the lens body 21 is 6 mm with the overall thickness varying depending on the optical power of the lens body 21. The holes 27 are approxiamtely 0.3 mm in diameter and are generally four in number positioned as shown in FIG. 1. The general thickness of each fixation loop members 23 is approximately 0.3 mm. The width of the arm portion 23A, elbow 23C and outward-convex portion 23D is approximately 0.3 mm. The outside radius of curvature of the elbow 23C is 0.8 mm. The inside radius of curvature of the elbow 23C is 0.5 mm. The length of the convex curvature of the outward-convex portion 23D is approxiamtely 4 mm with a total overall length of approximately 4.5 mm measuring from the free end 23E to the elbow 23C. The width of the base 23B joining the fixation loop member 23 to the optic lens body 21 will vary according to the demands of flexibility required. Arm position 23A is relatively straight defining an acute angle with outward-convex portion 23D. In one embodiment the lens is cut (and polished) from a single piece of plastic material such as polymethylmethacrylate whereby the arm portions 23A and outward-convex portions 23D are flexible and resilient. The overall design of the fixation loop members 23 provides flexibility of the arm portions 23A about the base junction 23B, at the elbows 23C and along the outward-convex portions 23D.

The specific curvatures of the fixation loop members 23 described and shown provide a unique combination of curves providing at the same time maximum flexibility with its attendant advantages along with maximum rigidity necessary for safe and secure fixation. The fixation along the outer edges 23D of the broad outward-convex portions 23D provides a broad area of tissue contact and fixation. The convex feature of the outer fixation edges 23D along with the junction of members 23D with the elbows 23C are particularly unique in that they allow for safer manipulation of the intraocular lens within the eye within either the anterior chamber or the posterior chamber, when manipulation is necessary for proper seating or adjustment within the eye. Particularly, "dialing" that is, spinning or turning of the lens within either the anterior chamber or posterior chamber is possible very safely due to the overall structure and flexibility of the lens, this particularly being more safe in this lens design than in any other lens design intended for both the anterior chamber and posterior chamber use.

Figure 6:
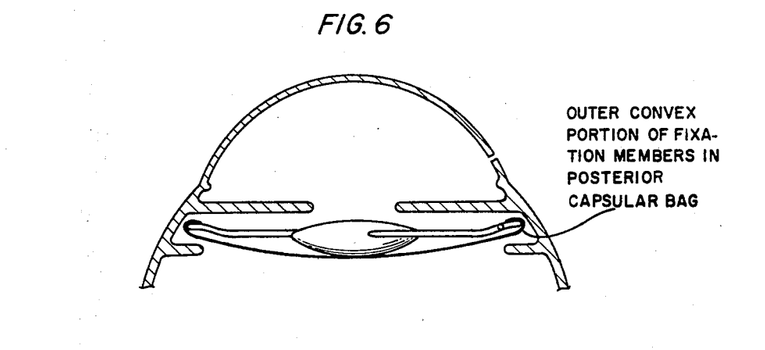
FIG. 6 is a partial simplified schematic sectional view of an eye with the lens of the present invention implanted in the posterior chamber with its fixation members in the posterior capsular bag.
Figure 7:
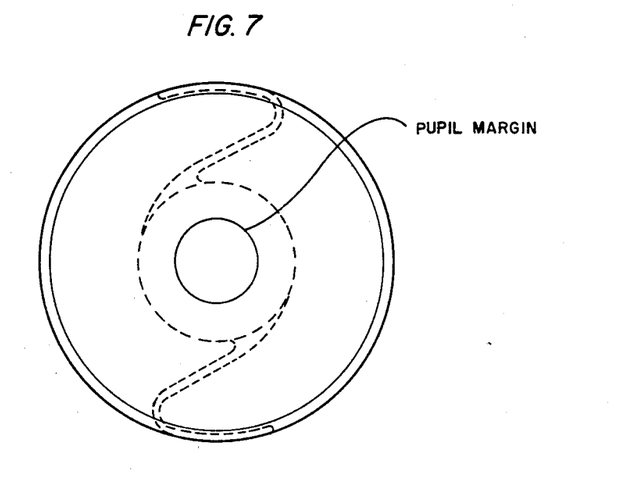
FIG. 7 is a front view of the lens as seen in position in the posterior chamber (behind the iris).

Referring now to FIGS. 3-7 there will be described implantation of the intraocular lens within the eye in either the anterior chamber or posterior chamber. In these Figs. the lens body is convex-convex. When the lens is implanted in the anterior chamber (See FIG. 3), the vaulting 23C' of the lens places the optical lens body 21 anterior to the plane of the iris. The outward-convex portion 23D is fixated or seated in the area of the scleral spur similar to the technique used in other available anterior lens designs. If the lens is implanted in the posterior chamber of the eye (See FIGS. 5 and 6) the vaulting 23C' of the lens places the optical lens body 21 more posterior than the outward-convex portions 23D of the fixation loop members 23, thereby urging the lens body 21 against the posterior capsule. Implantation of the lens device in the posterior chamber can be done with the outward-convex portions 23D of the fixation loop members 23 being placed either in the cilliary sulcus (FIG. 5) or in the capsular bag (FIG. 6).

Any of the above techniques may be performed as a primary or secondary surgical procedure. Implantation of the intraocular lens in either the anterior or posterior chamber of the eye may be done after either extracapsular or intracapsular lens extraction.

Figure 8:
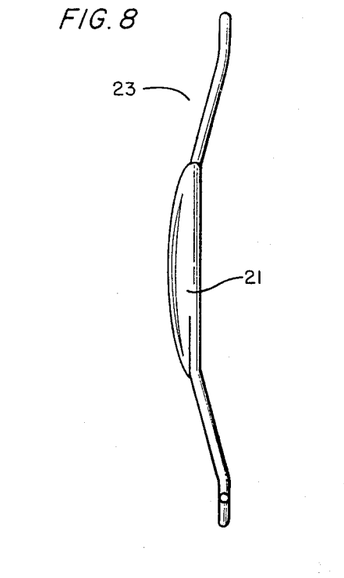
FIG. 8 is a side view of a modified lens having gradual vaulting of its fixation members.
Figure 9:
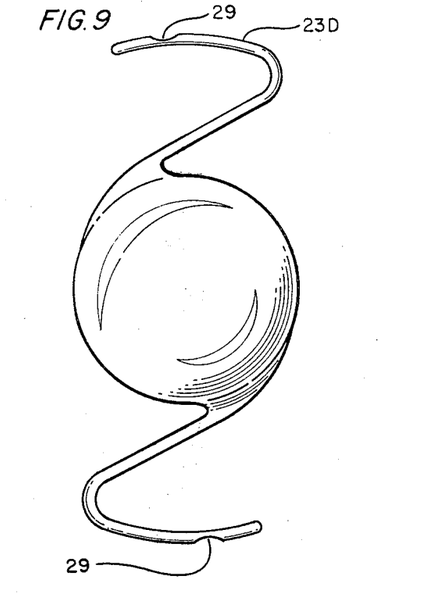
FIG. 9 is a front plan view of the lens of FIG. 1 having small indentations along the outward-convex curve of the fixation members.
Figure 10:
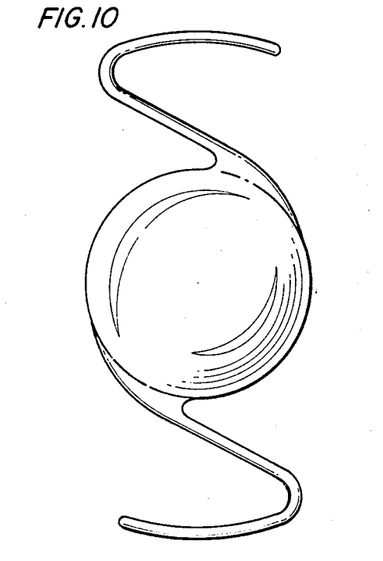
FIG. 10 is a front plan view of a modified lens having its fixation members arranged on opposite sides of the lens body and extending in opposite directions from that shown in FIG. 1.
Figure 11:
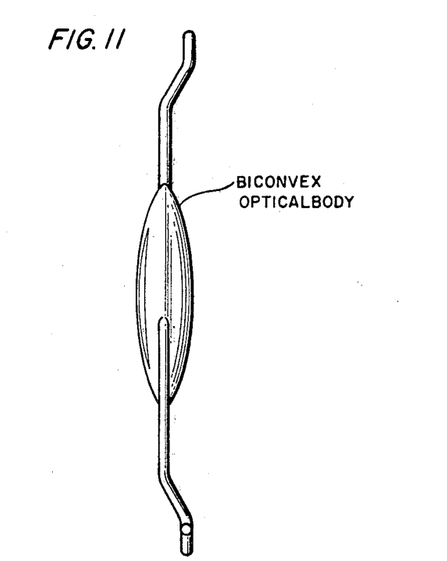
FIG. 11 is a side view of a convex-convex lens body.

Referring to FIG. 8, the vaulting provided by the step off of the fixation loop members 23 may be provided by a gradual sloping of the members 23 from their junction with the lens body 21, rather than a sharp step off. Referring to FIG. 9, small indentations 29 may be formed anywhere along the convex curve of outward-convex portions 23D to provide for easier manipulation of the loop members 23. Referring to FIG. 10, the loop members 23 may be arranged such that the elbows point in a counterclockwise direction rather than in a clockwise directions when viewing the lens from a given plan view. The holes 27 may vary in number and position on the lens body 21 or may be formed in the bases 23B of the loop members 23. The optical lens body 21 may be planar-convex (FIG. 1), or convex-convex (FIG. 11). In addition the intraocular lens may be formed of separate pieces of suitable plastic with the fixation loop members 23 formed separately from the lens body 21 and mechanically attached to the lens body 21.

I claim:

1. An intraocular insert suitable for use as an artificial lens implant in the anterior chamber or posterior chamber of a human eye, comprising:

a lens body having a peripherial edge portion defining a circle, said lens body having first and second position fixation members extending from opposite sides of the periphery of said lens body, each of said first and second position fixation members comprising an arm portion having a base joined to the periphery of said lens body with said arm portion extending from said lens body, an elbow, and an elongated outward-convex seating portion having a first end joined to said arm portion by said elbow and an opposite free end extending in a direction such that said elongated outward-convex seating portion is outward of said arm portion relative to said lens body, the two bases of said arm portions of said first and second position fixation members being located on opposite sides of said lens body to allow a first plane coinciding with and passing through the axis of said lens body to pass through said two bases, said arm portions of said first and second position fixation members extending from said lens body in opposite directions relative to each other, said two bases of said arm portions being further located on opposite sides of a second plane coinciding with and passing through the axis of said lens body, said second plane also passing through said arm portions and through said outward-convex seating portions, each arm portion of each of said position fixation members crossing said second plane from its base and has its elbow including the inside edge of its elbow located on a side of said second plane opposite the side on which its base is located, said elongated outward-convex seating portions extending from their elbows respectively in opposite directions relative to each other, the curvature of the elbow of each of said position fixation members being much sharper than the curvature of its outward-convex seating portion, the distance between the elbow and the free end of each of said position fixation members being greater than the distance between its outward-convex seating portion and the nearest edge of said lens body, each position fixation member being relatively small in cross-section and resilient such that its arm portion and elbow may be moved toward said lens body and its elongated outward-convex seating portion may be moved toward its arm portion and hence toward said lens body each of said outward-convex seating portions providing a broad area of tissue contact and fixation when said insert is implanted in the eye.

2. The intraocular insert of claim 1, wherein:

each elongated outward-convex seating portion has a length greater than the radius of said circle of said lens body, the curvature of each of said elongated outward-convex seating portions being relatively broad compared to the radius of curvature of said circle of said lens body.

3. The intraocular insert of claims 1 or 2, wherein:
said insert is formed of a single piece of plastic material.

4. The intraocular insert of claims 1 or 2, wherein:
each arm portion comprises a generally straight portion generally parallel to a line tangent to said lens body.

5. The intraocular insert of claims 1 or 2, wherein:
each arm portion comprises a straight portion which defines an angle of about 90° relative to said first plane passing through the axis of said lens body and through said two bases of said first and second position fixation members.

6. The intraocular insert of claims 1 or 2, wherein:
each elongated outward-convex seating portion has a single outward-convex seating curve.

7. The intraocular insert of claims 1 or 2, wherein:
each arm portion has a major portion of its length located between its outward-convex portion and said lens body when seen from a plan view of said intraocular insert.

8. The intraocular insert of claims 1 or 2, wherein:
each arm portion comprises a generally straight portion generally parallel to a line tangent to said lens body, each arm portion has a major portion of its length located between its outward-convex portion and said lens body when seen from a plan view of said intraocular insert.

9. The intraocular insert of claims 1 or 2 wherein:
each arm portion comprises a straight portion which defines an angle of about 90° relative to said first plane passing through the axis of said lens body and through said two bases of said first and second position fixation members,
each arm portion has a major portion of its length located between its outward-convex portion and said lens body when seen from a plan view of said intraocular insert.

10. The intraocular insert of claims 1 or 2, wherein:
each arm portion comprises a straight portion generally parallel to a line tangent to said lens body,
each arm portion has a major portion of its length located between its outward-convex portion and said lens body when seen from a plan view of said intraocular insert,
each elongated outward-convex seating portion has a single outward-convex seating curve.

11. The intraocular insert of claims 1 or 2, wherein:
each arm portion comprises a straight portion which defines an angle of about 90° relative to said first plane passing through the axis of said lens body and through said two bases of said first and second position fixation members,
each arm portion has a major portion of its length located between its outward-convex portion and said lens body when seen from a plan view of said intraocular insert,
each elongated outward-convex seating portion has a single outward-convex seating curve.

12. The intraocular insert of claims 1 or 2, wherein:
said first and second position fixation members are of similar shape but asymmetrically arranged relative to said lens body.

13. The intraocular insert of claim 1, wherein:
in a plane perpendicular to the axis of said lens body, each position fixation member is flexible about the junction of its base with the periphery of said lens body,
in a plane perpendicular to the axis of said lens body, each position fixation member is flexible at its elbow,
in a plane perpendicular to the axis of said lens body, each position fixation member is flexible along its outward-convex seating portion.

14. The intraocular insert of claim 1, wherein:
each of said position fixation members, including its arm portion, elbow, and the major portion of its outward-convex seating portion has a cross sectional width about equal to its cross sectional thickness.

15. The intraocular insert of claim 1, wherein:
said elbows of said first and second position fixation members are located such that said first plane passing through said two bases does not pass through said elbows.

16. An intraocular insert suitable for use as an artificial lens implant in the anterior chamber or posterior chamber of a human eye, comprising:
a lens body having first and second position fixation members extending from opposite sides of the periphery of said lens body,
each of said first and second position fixation members comprising an arm portion having a base joined to the periphery of said lens body with said arm portion extending from said lens body, an elbow, and an elongated outward-convex seating portion having a first end joined to said arm portion by said elbow, and an opposite free end, said elongated outward-convex seating portion being located outward of said arm portion relative to said lens body,
the two bases of said arm portions of said first and second position fixation members being located on opposite sides of said lens body and on opposite sides of a plane coinciding with and passing through the axis of said lens body, said plane also passing through said arm portions and through said outward-convex seating portions,
each arm portion of each of said position fixation members crosses said plane from its base and has its elbow including the inside edge of its elbow located on a side of said plane opposite the side on which its base is located,
each outward-convex seating portion of each of said position fixation members extends from its elbow in a direction such that it crosses said plane with its free end located on the side of said plane on which its base is located,
the curvature of the elbow of each of said position fixation members is much sharper than the curvature of its outward-convex seating portion,
each position fixation member being relatively small in cross-section and resilient such that its arm portion may be moved toward said lens body and its elongated outward-convex seating portion may be moved toward its arm portion and hence toward said lens body,
each of said outward-convex seating portions providing a broad area of tissue contact and fixation when said insert is implanted in the eye.

17. The intraocular insert of claim 16, wherein:
said lens body has a peripheral edge portion defining a circle,
the distance between each outward-convex seating portion and said lens body is less than the diameter of said circle of said lens body.

18. The intraocular insert of claim 16, wherein:
said lens body has a peripheral edge portion defining a circle,
the distance between the elbow and the free end of each of said fixation position members is greater than the radius of said circle of said lens body.

19. The intraocular insert of claim 16, wherein:
in a plane perpendicular to the axis of said lens body, each position fixation member is flexible about the junction of its base with the periphery of said lens body,
in a plane perpendicular to the axis of said lens body, each position fixation member is flexible at its elbow,
in a plane perpendicular to the axis of said lens body, each position fixation member is flexible along its outward-convex seating portion.

20. The intraocular insert of claim 16, wherein:
the distance between the elbow and the free end of each of said position fixation members is greater than the distance between its outward-convex seating portion and the nearest edge of said lens body.

21. The intraocular insert of claim 16, wherein:

each of said position fixation members, including its arm portion, elbow, and the major portion of its outward-convex seating portion has a cross sectional width about equal to its cross sectional thickness.

22. The intraocular insert of claim 16, wherein:
said plane passing through the axis of said lens body passes through about the mid-points of said outward-convex seating portions between their elbows and their free ends and is defined as a central plane,
the peripheral edge of said lens body on opposite sides of said central plane is tangential to two planes parallel to said central plane,
the elbow of said first position fixation member including its inside edge is closer to one of said two planes than to said central plane,
the elbow of said second position fixation member including its inside edge is closer to the other of said two planes than to said central plane,
the free end of said first position fixation member is closer to said other of said two planes than to said central plane,
the free end of said second position fixation member is closer to said one of said two planes than to said central plane.

23. The intraocular insert of claim 16, wherein:
each arm portion has an inside edge facing a portion of said lens body,
the junction of said inside edge of each arm portion with said lens body being located on the same side of said plane as its base.

24. The intraocular insert of claim 16, wherein:
in a plane perpendicular to the axis of said lens body, each position fixation member is flexible about the junction of its base with the periphery of said lens body,
in a plane perpendicular to the axis of said lens body, each position fixation member is flexible at its elbow,
in a plane perpendicular to the axis of said lens body, each position fixation member is flexible along its outward-convex seating portion,
the distance between the elbow and the free end of each of said position fixation members is greater than the distance between its outward-convex seating portion and the nearest edge of said lens body.

25. The intraocular insert of claim 24, wherein:
said plane passing through the axis of said lens body passes through about the mid-points of said outward-convex seating portions between their elbows and their free ends and is defined as a central plane,
the peripheral edge of said lens body on opposite sides of said central plane is tangential to two planes parallel to said central plane,
the elbow of said first position fixation member including its inside edge is closer to one of said two planes than to said central plane,
the elbow of said second position fixation member including its inside edge is closer to the other of said two planes than to said central plane,
the free end of said first position fixation member is closer to said other of said two planes than to said central plane,
the free end of said second position fixation member is closer to said one of said two planes than to said central plane.

26. The intraocular insert of claim 23, wherein:
in a plane perpendicular to the axis of said lens body, each position fixation member is flexible about the junction of its base with the periphery of said lens body,
in a plane perpendicular to the axis of said lens body, each position fixation member is flexible at its elbow,
in a plane perpendicular to the axis of said lens body, each position fixation member is flexible along its outward-convex seating portion,
the distance between the elbow and the free end of each of said position fixation members is greater than the distance between its outward-convex seating portion and the nearest edge of said lens body.

27. The intraocular insert of claim 26, wherein:
said plane passing through the axis of said lens body passes through about the mid-points of said outward-convex seating portions between their elbows and their free ends and is defined as a central plane,
the peripheral edge of said lens body on opposite sides of said central plane is tangential to two planes parallel to said central plane,
the elbow of said first position fixation member including its inside edge is closer to one of said two planes than to said central plane,
the elbow of said second position fixation member including its inside edge is closer to the other of said two planes than to said central plane,
the free end of said first position fixation member is closer to said other of said two planes than to said central plane,
the free end of said second position fixation member is closer to said one of said two planes than to said central plane.

28. An intraocular insert suitable for use as an artificial lens implant in the anterior chamber or posterior chamber of a human eye, comprising:
a lens body having first and second position fixation members extending from opposite sides of the periphery of said lens body,
each of said first and second position fixation members comprising an arm portion having a base joined to the periphery of said circular lens body with said arm portion extending from said lens body, an elbow, and an elongated outward-convex seating portion having a first end joined to said arm portion by said elbow, and an opposite free end, said elongated outward-convex seating portion being located outward of said arm portion relative to said lens body,
the two bases of said arm portions of said first and second position fixation members being located on opposite sides of said lens body to allow a first plane coinciding with and passing through the axis of said lens body to pass through said two bases,
the two bases of said arm portions of said first and second position fixation members being located on opposite sides of and equally spaced from a second plane coinciding with and passing through the axis of said lens body, said second plane also passing through said arm portions and through said outward-convex seating portions,
said arm portions of said first and second position fixation members extending from said lens body in opposite directions relative to each other, said elongated outward-convex seating portions extending from their elbows respectively in opposite directions relative to each other, each arm portion of each of said position fixation members crosses said second plane from its base and has its elbow including the inside edge of its elbow located on a side of said second plane opposite the side on which its base is located, each outward-convex seating portion of each of said position fixation members extends from its elbow in a direction such that it crosses said second plane with its free end located on the side of said second plane on which its base is located, each position fixation member being relatively small in cross-section and resilient such that its arm portion and elbow may be moved toward said lens body and its elongated outward-convex seating portion may be moved toward its arm portion and hence toward said lens body, each of said outward-convex seating portions providing a broad area of tissue contact and fixation when said insert is implanted in the eye.

29. The intraocular insert of claim 28, wherein:
the curvature of the elbow of each of said position fixation members is much sharper than the curvature of its outward-convex seating portion.

30. The intraocular insert of claim 28, wherein:
said lens body has a peripheral edge portion defining a circle,
the distance between each outward-convex seating portion and said lens body is less than the diameter of said circle of said lens body.

31. The intraocular insert of claim 28, wherein:
said lens body has a peripheral edge portion defining a circle,
the distance between the elbow and the free end of each of said fixation position members is greater than the radius of said circle of said lens body.

32. The intraocular insert of claim 28, wherein:
in a plane perpendicular to the axis of said lens body, each position fixation member is flexible about the junction of its base with the periphery of said lens body,
in a plane perpendicular to the axis of said lens body, each position fixation member is flexible at its elbow,
in a plane perpendicular to the axis of said lens body, each position fixation member is flexible along its outward-convex seating portion.

33. The intraocular insert of claim 28, wherein:
the distance between the elbow and the free end of each of said position fixation members is greater than the distance between its outward-convex seating portion and the nearest edge of said lens body.

34. The intraocular insert of claim 28, wherein:
each of said position fixation members, including its arm portion, elbow, and the major portion of its outward-convex seating portion has a cross sectional width about equal to its cross sectional thickness.

35. The intraocular insert of claim 28, wherein:
the peripheral edge of said lens body on opposite sides of said second plane is tangential to two planes parallel to said second plane,
the elbow of said first position fixation member including its inside edge is closer to one of said two planes than to said second plane,
the elbow of said second position fixation member including its inside edge is closer to the other of said two planes than to said second plane,
the free end of said first position fixation member is closer to said other of said two planes than to said second plane,
the free end of said second position fixation member is closer to said one of said two planes than to said second plane.

36. The intraocular insert of claim 28, wherein:
each arm portion has an inside edfge facing a portion of said lens body,
the junction of said inside edge of each arm portion with said lens body being located on the same side of said second plane as its base.

37. The intraocular insert of claims 28, wherein:
in a plane perpendicular to the axis of said lens body, each position fixation member is flexible about the junction of its base with the periphery of said lens body,
in a plane perpendicular to the axis of said lens body, each position fixation member is flexible at its elbow,
in a plane perpendicular to the axis of said lens body, each position fixation member is flexible along its outward-convex seating portion,
the distance between the elbow and the free end of each of said position fixation members is greater than the distance between its outward-convex seating portion and the nearest edge of said lens body.

38. The intraocular insert of claim 37, wherein:
the peripheral edge of said lens body on opposite sides of said second plane is tangential to two planes parallel to said second plane,
the elbow of said first position fixation member including its inside edge is closer to one of said two planes than to said second plane,
the elbow of said second position fixation member including its inside edge is closer to the other of said two planes than to said second plane,
the free end of said first position fixation member is closer to said other of said two planes than to said second plane,
the free end of said second position fixation member is closer to said one of said two planes than to said second plane.

39. The intraocular insert of claim 36, wherein:
in a plane perpendicular to the axis of said lens body, each position fixation member is flexible about the junction of its base with the periphery of said lens body,
in a plane perpendicular to the axis of said lens body, each position fixation member is flexible at its elbow,
in a plane perpendicular to the axis of said lens body, each position fixation member is flexible along its outward-convex seating portion,
the distance between the elbow and the free end of each of said position fixation members is greater than the distance between its outward-convex seating portion and the nearest edge of said lens body.

40. The intraocular insert of claim 39, wherein:
the peripheral edge of said lens body on opposite sides of said second plane is tangential to two planes parallel to said second plane,
the elbow of said first position fixation member including its inside edge is closer to one of said two planes than to said second plane, the elbow of said second position fixation member including its inside edge is closer to the other of said two planes than to said second plane, the free end of said first position fixation member is closer to said other of said two planes than to said second plane, the free end of said second position fixation member is closer to said one of said two planes than to said second plane.

41. The intraocular insert of claim 28, wherein:

an acute angle is formed by a plane extending between the free end of each position fixation member and its elbow and a plane extending between its elbow and its base.

42. An intraocular insert suitable for use as an artificial lens implant in the anterior chamber or posterior chamber of a human eye, comprising:

a lens body having first and second position fixation members extending from opposite sides of the periphery of said lens body, each of said first and second position fixation members comprising an arm portion having a base joined to the periphery of said lens body with said arm portion extending from said lens body, an elbow, and an elongated outward-convex seating portion having a first end joined to said arm portion by said elbow, and a free end, said elongated outward-convex seating portion being located outward of said arm portion relative to said lens body, the two bases of said arm portions of said first and second position fixation member being located on opposite sides of said lens body and on opposite sides of a plane passing through said lens body, through said arm portions and through about the midpoints of said outward-convex seating portions between their elbows and their free ends, each arm portion of each of said position fixation members crosses said plane from its base and has its elbow including the inside edge of its elbow located on a side of said plane opposite the side on which its base is located, each outward-convex seating portion of each of said position fixation members extends from its elbow in a direction such that it crosses said plane with its free end located on the side of said plane on which its base is located, the curvature of the elbow of each of said position fixation members is much sharper than the curvature of its outward-convex seating portion, each position fixation member being relatively small in cross-section and resilient such that its arm portion may be moved toward said lens body and its elongated outward-convex seating portion may be moved toward its arm portion and hence toward said lens body, each of said outward-convex seating portions providing a broad area of tissue contact and fixation when said insert is implanted in the eye.

43. The intraocular insert of claim 42, wherein:

the distance between the elbow and the free end of each of said position fixation members is greater than the distance between its outward-convex seating portion and the nearest edge of said lens body.

44. The intraocular insert of claim 42, wherein:

said plane passing through said lens body is defined as a central plane, the peripheral edge of said lens body on opposite sides of said central plane is tangential to two planes parallel to said central plane, the elbow of said first position fixation member including its inside edge is closer to one of said two planes than to said central plane, the elbow of said second position fixation member including its inside edge is closer to the other of said two planes than to said central plane, the free end of said first position fixation member is closer to said other of said two planes than to said central plane, the free end of said second position fixation member is closer to said one of said two planes than to said central plane.

45. The intraocular insert of claim 43, wherein:

said plane passing through said lens body is defined as a central plane, the peripheral edge of said lens body on opposite sides of said central plane is tangential to two planes parallel to said central plane, the elbow of said first position fixation member including its inside edge is closer to one of said two planes than to said central plane, the elbow of said second position fixation member including its inside edge is closer to the other of said two planes than to said central plane, the free end of said first position fixation member is closer to said other of said two planes than to said central plane, the free end of said second position fixation member is closer to said one of said two planes than to said central plane.

46. The intraocular insert of either of claims 42, 43, 44, or 45, wherein:

said arm portions of said first and second position fixation members extend from said lens body in opposite directions relative to each other, said elongated outward-convex seating portions extend from their elbows respectively in opposite directions relative to each other.

* * * * *